United States Patent [19]

Mizutani et al.

[11] 4,359,583
[45] Nov. 16, 1982

[54] ANTIBIOTICS TM-531 B AND TM-531 C

[75] Inventors: Taku Mizutani, Ageo; Michio Yamagishi, Tokorozawa; Kazutoshi Mizoue, Saitama; Akira Kawashima, Tokyo; Sadafumi Omura, Ageo; Noboru Otake, Yokohama; Haruo Seto, Hachioji, all of Japan

[73] Assignee: Taisho Pharmaceutical Co., Ltd., Tokyo, Japan

[21] Appl. No.: 302,017

[22] Filed: Sep. 15, 1981

[30] Foreign Application Priority Data

Sep. 16, 1980 [JP] Japan .................................. 55-128107
Sep. 18, 1980 [JP] Japan .................................. 55-129576

[51] Int. Cl.³ ............................................ C07D 309/10
[52] U.S. Cl. .................................... 549/343; 424/283
[58] Field of Search .................. 260/345.7 R; 549/343

[56] References Cited

U.S. PATENT DOCUMENTS 4,269,971 5/1981 Yamagishi et al. .......... 260/345.7 R

*Primary Examiner*—Nicky Chan

*Attorney, Agent, or Firm*—Sughrue, Mion, Zinn, Macpeak & Seas

[57] ABSTRACT

The novel antibiotics represented by the formula

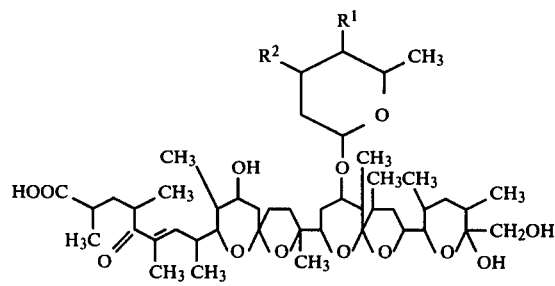

wherein either (a) $R^1$ is hydroxy and $R^2$ is hydrogen, or (b) $R^1$ is methoxy and $R^2$ is hydroxy, and the salt thereof, are produced by the cultivation of the organism *Streptomyces hygroscopicus* TM-531 under aerobic conditions. They are separated from coproduced Antibiotic TM-531 as disclosed in U.S. Pat. No. 4,269,971 and from each other by chromatography on silica gel.

3 Claims, 6 Drawing Figures

ANTIBIOTICS TM-531 B AND TM-531 C

FIELD OF THE INVENTION

This invention relates to new antibiotics produced by *Streptomyces hygroscopicus* TM-531.

BACKGROUND OF THE INVENTION

Antibiotic TM-531, which is produced by culturing the organism *Streptomyces hygroscopicus* TM-531, is described in U.S. Pat. No. 4,269,971. The structural formula of Antibiotic TM-531 is shown by the formula

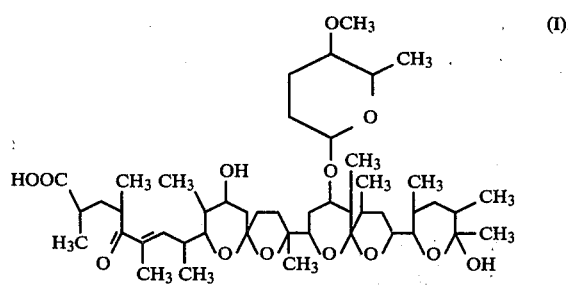

The present invention is concerned with new antibiotic compounds related to Antibiotic TM-531, which compounds have the formula

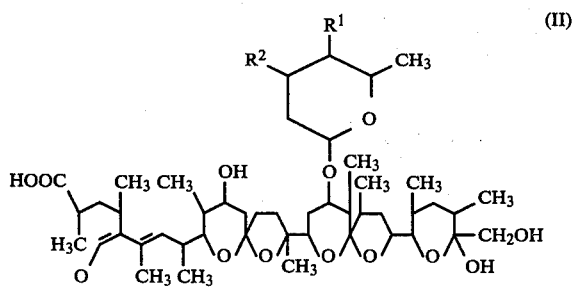

wherein either (a) $R^1$ is hydroxy and $R^2$ is hydrogen, or (b) $R^1$ is methoxy and $R^2$ is hydroxy, and the salt thereof.

The compounds of the present invention inhibit gram-positive bacteria, plant pathogenic microorganism and protozoa.

DETAILED DESCRIPTION OF THE INVENTION

Figure 1:
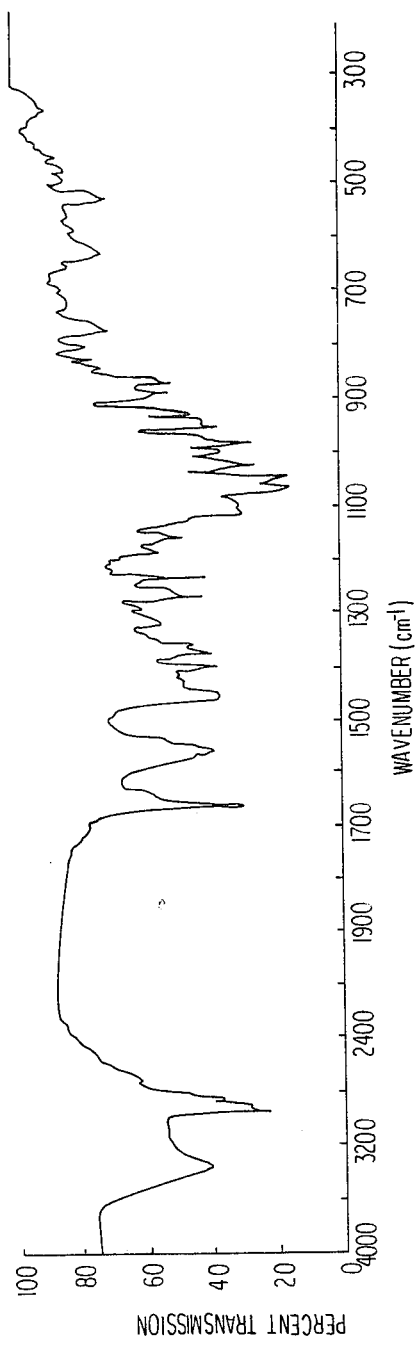
FIGS. 1 and 2 show infrared absorption spectra of Antibiotics TM-531 B and TM-531 C, respectively, as determined by the KBr disc method.

The compounds of formula (II) are coproduced in small amounts with Antibiotic TM-531 and dianemycin as described in J. Antibiotics, 33,137 (1980) by culturing *Streptomyces hygroscopicus* TM-531 under aerobic conditions. For convenience, the compounds of formula (II) wherein $R^1$ is hydroxy and $R^2$ is hydrogen, and wherein $R^1$ is methoxy and $R^2$ is hydroxy will be identified hereinafter as Antibiotics TM-531 B and TM-531 C, respectively.

The salts of the compounds of formula (II) include salts such as sodium salt, potassium salt, calcium salt, iron salt, ammonium salt and the like. These salts can be obtained, for example, by treating the compound of formula (II) with the corresponding base in a conventional manner.

*Streptomyces hygroscopicus* TM-531 has been deposited under the name of Streptomyces TM-531 at Fermentation Research Institute, Agency of Industrial Science and Technology, Japan as FERM-P 4737 on Nov. 29, 1978 and at American Type Culture Collection, as ATCC 31590, the cultivation and detailed description of which are disclosed in U.S. Pat. No. 4,269,971.

Production of Antibiotics TM-531 B and TM-531 C can be generally conducted according to the general procedures for producing antibiotics, and performed by culturing Antibiotics TM-531 B and TM-531 C producing bacterium in a medium containing various nutrients under aerobic conditions. The medium is preferably a liquid medium, mainly comprising carbon sources, nitrogen sources and inorganic salts, and an antifoaming agent, vitamins, precursor materials, etc. may be further added as needed. The pH of the medium is adjusted to 7 or its vicinity.

Examples of the carbon sources are glucose, maltose, starch, dextrin, glycerin, peanut oil, etc. which cn be used either alone or as a mixture thereof. Examples of the nitrogen sources are peptone, meat extract, soybean meal, oatmeal, corn steep liquor, urea, ammonium salt, etc. which can be used either alone or as a mixture thereof. Examples of the inorganic salts are calcium carbonate, sodium chloride, ferric sulfate, manganese chloride, etc. which can be used either alone or as a mixture thereof.

As the antifoaming agents, a silicone compound, etc. may be employed.

The method for cultivation is suitably aerobic culture such as shake culture, submerged aerated culture, etc., and it is carried out at pH 7 or its vicinity and at a temperature of about 25° to 40° C., desirably at 28° to 30° C.

Antibiotics TM-531 B and TM-531 C produced by cultivation may be isolated, for example, in the following manner.

The culture broth at the end of fermentation is centrifuged to separate into the supernatant and the mycelium.

The active substances in the supernatant are extracted with a water-insoluble organic solvent such as ethyl acetate, benzene, chloroform, etc. or adsorbed onto an adsorbing resin and then eluted with an organic solvent such as an alcohol, acetone, etc. If necessary, after concentration, it is also possible to further perform extraction using an appropriate organic solvent.

The active substances in the mycelium are extracted with an organic solvent such as an alcohol, acetone, etc. After concentration, the extract is transferred and dissolved in the same kind of solvent as the extracting solvent for the supernatant as described above.

The supernatant extract and the mycelium extract are combined and concentrated under reduced pressure. This concentrate is dissolved in benzene, and the active substances are adsorbed onto a silica gel column, through which an organic solvent such as benzene, ethyl acetate, etc. is passed to elute and remove Antibiotic TM-531 and dianemycin present in the active substances.

The remaining active substances are eluted with an organic solvent such as acetone, etc. and, after distilling off the solvent, dissolved in a mixed solvent of n-hexane-acetone (4:1 by volume), and adsorbed again onto a silica gel column.

After washing this column with a mixed solvent of n-hexane-acetone (4:1 by volume), the active substances are eluted using a mixed solvent of n-hexane-acetone (6:4 by volume). Antibiotics TM-531 B and TM-531 C are contained in the fractions from 1 to 1.5 and from 2 to 5 times the volume of the bed (confirmed by thin layer chromatography), respectively. These two fractions are separately collected and purified in a conventional manner to give Antibiotics TM-531 B and TM-531 C, respectively, as crystals. If necessary, for purification or use, Antibiotics TM-531 B and TM-531 C can be converted into the salts thereof as described above.

Antibiotics TM-531 B and TM-531 C, which are the object substances of this invention, have been confirmed to have the following structural formulae by analyzing their elemental analysis, molecular weight, ultraviolet absorption spectrum, $^1$H-NMR spectrum and $^{13}$C-NMR spectrum. Further, their physicochemical properties and anti-microbial activity are also set forth below:

(I) TM-531 B
(1) Structural formula:

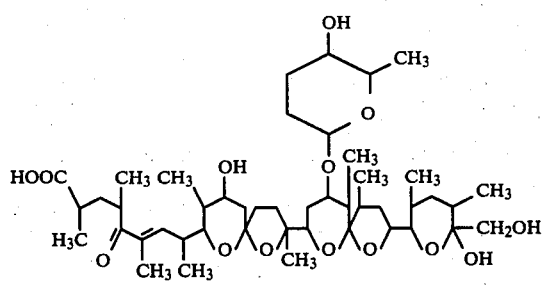

Figure 3:
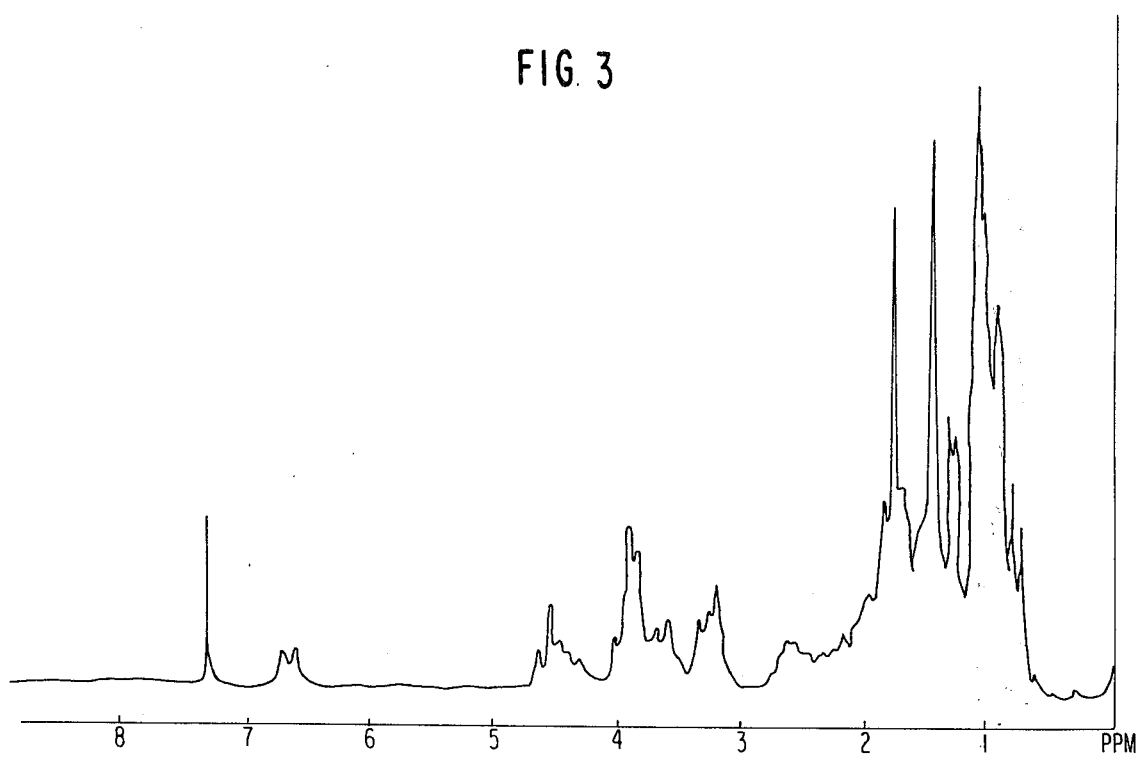
FIGS. 3 and 5 show $^1$H-NMR and $^{13}$C-NMR spectra, respectively, of Antibiotic TM-531 B as determined in CDCl$_3$ to which deutero methanol is added.
Figure 5:
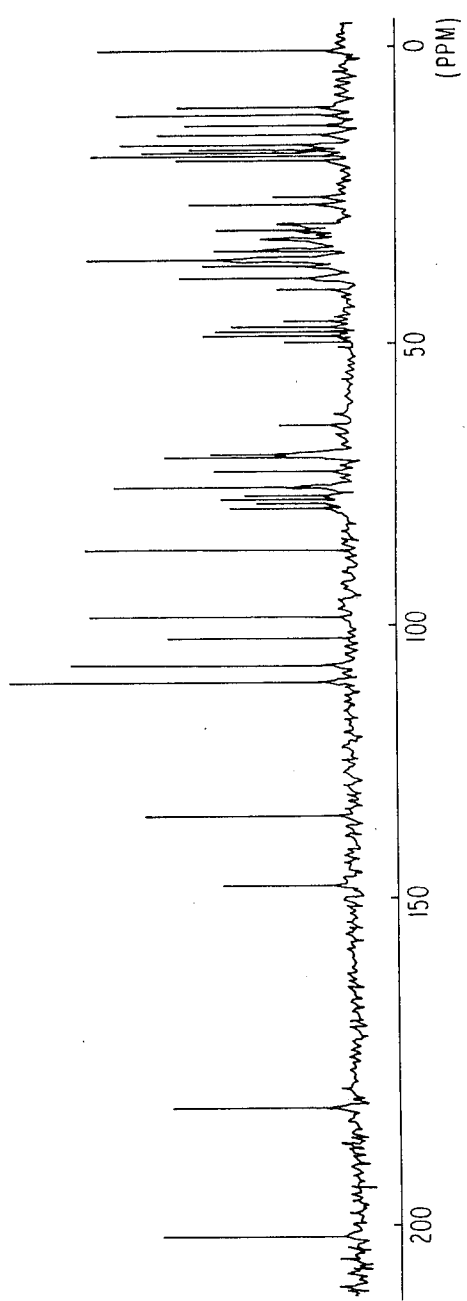

(2) Physicochemical properties (measured as the sodium salt of TM-531 B)
  (a) Elemental analysis for $C_{46}H_{75}O_{14}Na$:
    Calculated (%): C 63.16, H 8.58, Na 2.63
    Found (%): C 62.99, H 8.71, Na 2.51
  (b) Molecular weight: 874
  (c) Melting point: 252.1–253.3° C.
  (d) Specific rotatory power:
    $[\alpha]_D^{26} = +37.8°$ (C = 0.5, methanol)
  (e) Ultraviolet absorption (methanol):
    $E_{1cm}^{1\%}$ (232 nm) = 160.0
  (f) Infrared absorption spectrum:
    The result obtained by measuring with a KBr disc is shown in FIG. 1.
  (g) Solubility in solvents: Insoluble in water; soluble in methanol, ethanol, acetone, ethyl acetate, n-hexane, chloroform and benzene.
  (h) Color reactions: Positive in the iodine reaction, the potassium permanganate reaction and the vanillin - sulfuric acid reaction.
  (i) Color of the substance: Colorless
  (j) $^1$H-NMR spectrum (at 100 MHz) and $^{13}$C-NMR spectrum (at 25.05 MHz):
    The results obtained by measurement in deutero chloroform to which deutero methanol is added are given in FIG. 3 and FIG. 5, respectively.
  (k) Classification of Nature (as to whether basic, acidic or neutral): Acidic
(3) Physiological Properties
  Antibiotic TM-531 B inhibits the growth of gram-positive bacteria, plant pathogenic microorganisms, protozoa as hog dysentery, coccidium, toxoplasma and trypanosoma. Antibiotic TM-531 B is ineffective against gram-negative bacteria and yeasts.
  Antibiotic TM-531 B is also effective in improving the feed efficiency when it is incorporated into feeds for poultry, hogs, etc.

(II) TM-531 C
(1) Structural formula:

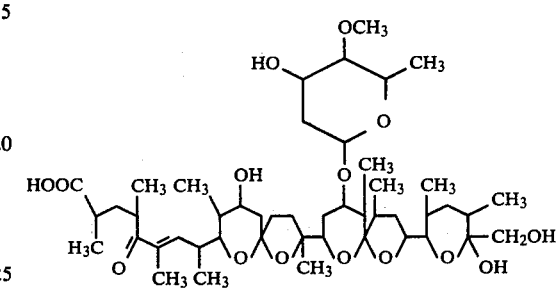

Figure 2:
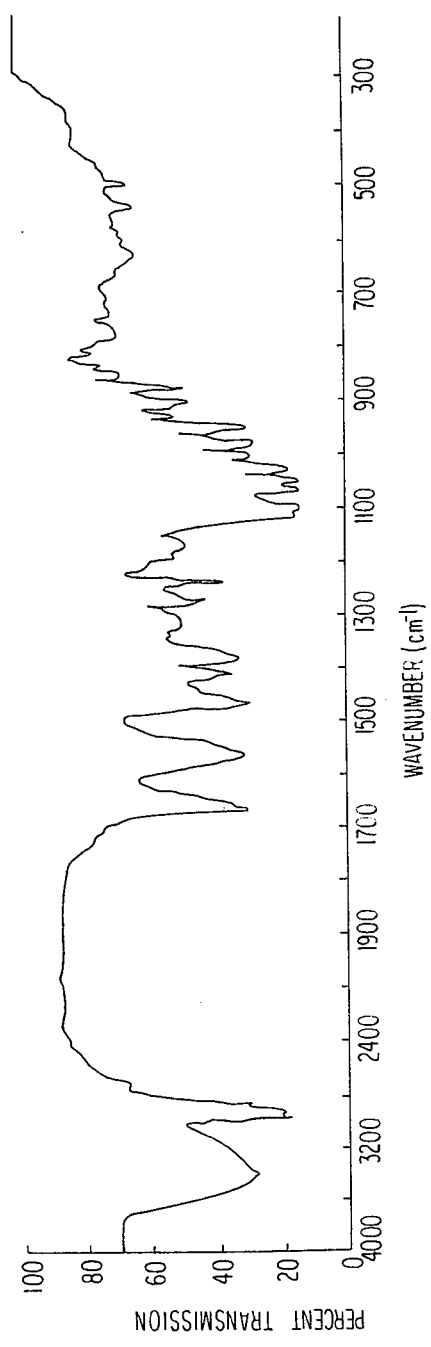
Figure 4:
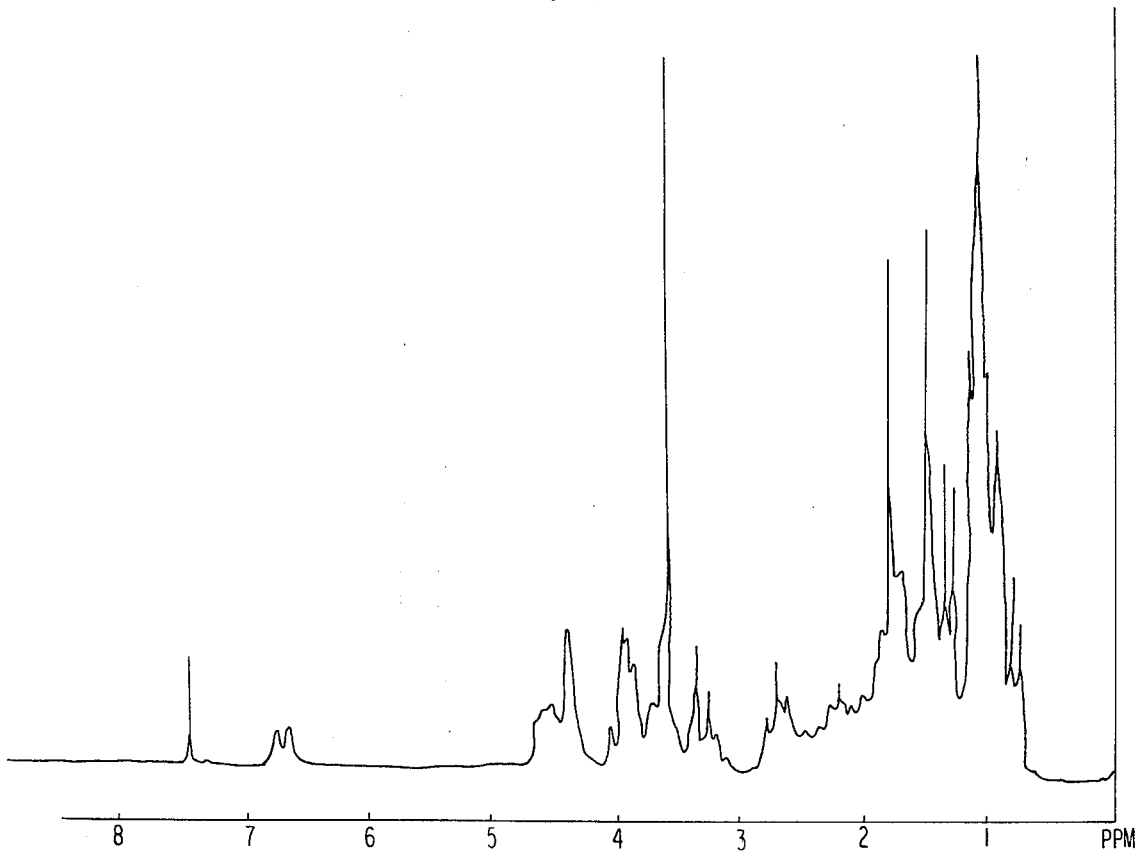
FIGS. 4 and 6 show $^1$H-NMR and $^{13}$C-NMR spectra, respectively, of Antibiotic TM-531 C as determined in CDCl$_3$ to which deutero methanol is added.
Figure 6:
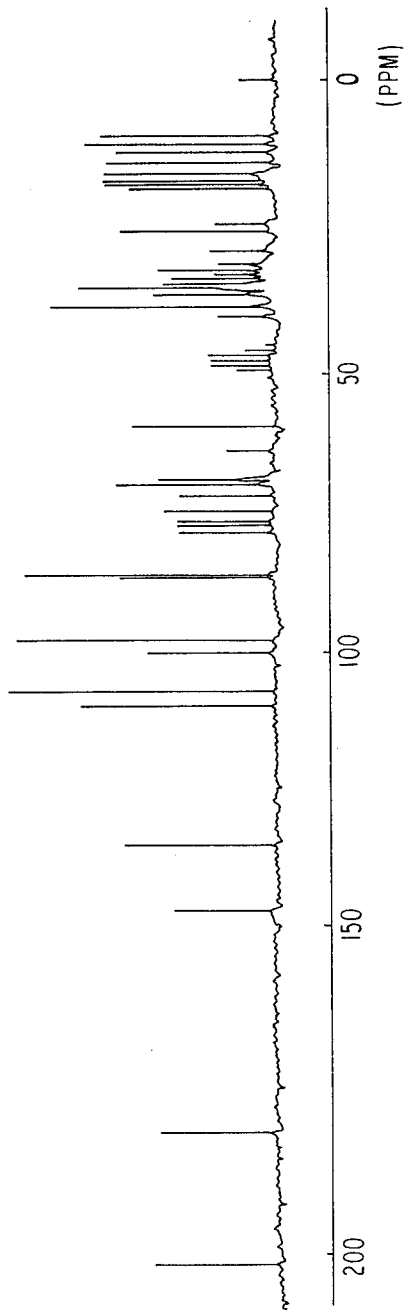

(2) Physicochemical properties (measured as the sodium salt of TM-531 C)
  (a) Elemental analysis for $C_{47}H_{77}O_{15}Na$
    Calculated (%): C 62.39, H 8.52, Na 2.54,
    Found (%): C 62.18, H 8.60, Na 2.44,
  (b) Molecular weight: 904
  (c) Melting point: 190.4–191.6° C.
  (d) Specific rotatory power:
    $[\alpha]_D^{26} = +27.4°$ (C = 0.5, methanol)
  (e) Ultraviolet absorption (methanol):
    $E_{1cm}^{1\%}$ (232 nm) = 146.6
  (f) Infrared absorption spectrum:
    The result obtained by measuring with a KBr disc is shown in FIG. 2.
  (g) Solubility is solvents: Insoluble in water; soluble in methanol, ethanol, acetone, ethyl acetate, n-hexane, chloroform and benzene.
  (h) Color reactions: Positive in the iodine reaction, the potassium permanganate reaction and the vanillin - sulfuric acid reaction.
  (i) Color of the substance: Colorless
  (j) $^1$H-NMR spectrum (at 100 MHz) and $^{13}$C-NMR spectrum (at 25.05 MHz):
    The results obtained by measurement in deutero chloroform to which deutero methanol is added are given in FIG. 4 and FIG. 6, repectively.
  (k) Classification of Nature (as to whether basic, acidic or neutral): Acidic
(3) Physiological Properties
  Antiobiotic TM-531 C inhibits the growth of gram-positive bacteria, plant pathogenic microorganisms, protozoa as hog dysentery, coccidium, toxoplasma and trypanosoma. Antibiotic TM-531 C is ineffective against gram-negative bacteria and yeasts.
  Antibiotic TM-531 C is also effective in improving the feed efficiency when it is incorporated into feeds for poultry, hogs, etc.

As described above, Antibiotics TM-531 B and TM-531 C are novel antibiotics which exhibit excellent growth inhibitory activity against gram-positive bacteria, plant pathogenic microorganism and protozoa and, therefore, are useful as pharmaceuticals, veterinary medicines and antimicrobial agents for plants. Further, Antibiotic TM-531 B and TM-531 C can be incorporated into feeds to prevent and treat the coccidiosis in domestic animals and poultry as well as to accelerate the growth of domestic animals and poultry.

The invention is more particularly illustrated by the following examples, including Test Example and Preparation which demonstrate the antibacterial activity of Antibiotics TM-531 B and TM-531 C. All percents, ratios, parts and the like are by weight, unless otherwise indicated.

Test Example

Using heart infusion agar as a medium the MIC (minimum inhibition concentration) of Antibiotics TM-531 B and TM-531 C against various bacteria were measured using an inoculum size of $10^6$ CFU/ml, to determine its antibacterial activity.

The results are shown in the following table.

| Antibacterial Activity | | |
|---|---|---|
| | MIC (mcg/ml) | |
| Bacteria Tested | TM-531 B | TM-531 C |
| *Staphylococcus aureus* FDA 209P | 6.25 | 12.5 |
| *Staphylococcus aureus* Smith | 12.5 | 25 |
| *Staphylococcus aureus* TPR-23 | 25 | 50 |
| *Staphylococcus epidermidis* TPR-25 | 12.5 | 25 |
| *Staphylococcus epidermidis* IID 866 | 12.5 | 25 |
| *Streptococcus faecalis* ATCC 8043 | 6.25 | 12.5 |
| *Bacillus subtilis* ATCC 6633 | 25 | 25 |
| *Bacillus licheniformis* | 6.25 | 12.5 |
| *Micrococcus luteus* NIHJ | 3.13 | 12.5 |
| *Escherichia coli* NIHJ C-2 | >100 | >100 |
| *Pseudomonas aeruginosa* IID 1052 | >100 | >100 |

EXAMPLE

An aseptic liquid medium comprising 2% glucose, 2% glycerin, 2% oatmeal, 0.5% peanut oil, 0.3% meat extract, 0.5% calcium carbonate, 0.3% sodium chloride, 0.04% ferric sulfate and 0.04% manganese chloride (pH 7.0) was inoculated with *Streptomyces hygroscopicus* TM-531 and shake culture was conducted at 30° C. for 72 hours. Three liters of the resulting culture broth was used as an inoculum and 200 liters of a medium having the same composition as above in a 250-liter fermentation tank was inoculated, and aerated stirred culture was conducted at 30° C. for 120 hours, during which time KS-66 (a silicone-type antifoaming agent, produced by Shin-etsu Chemical) was added as an antifoaming agent, if necessary, depending on the condition. Two hundred liters of the cultural broth thus obtained was centrifuged to separate into the mycelium and the supernatant.

The mycelium was extracted with 20 liters of acetone twice, and the supernatant was adsorbed onto Amberlite XAD-8 (commodity name, produced by Rohm and Haas) and, after washing, eluted with acetone.

These acetone extracts and acetone eluate were combined and concentrated under reduced pressure. The obtained residue was extracted with 2 liters of ethyl acetate twice, the extracts were combined, dried over sodium sulfate, and the solvent was distilled off under reduced pressure to obtain about 123 g of an oil.

This oil was then dissolved in 0.5 liter of benzene, and adsorbed onto a silica gel column [Wakogel C-200 (commodity name, produced by Wako Junyaku); 2 liters] which had been prepared using benzene. After washing the column with 5 liters of benzene, the fractions obtained by eluting with 5 liters of ethyl acetate were removed, and then 5 liters of acetone was passed through the column.

The acetone fractions were collected, the solvent was removed, the residue obtained was dissolved in 0.1 liter of a mixed solvent of n-hexane-acetone (4:1 by volume) and adsorbed onto a silica gel column (Wakogel C-200; 0.5 liter) which had been prepared using the same mixed solvent as above. Subsequently, after passing 1.5 liters of the same solvent as above, a mixed solvent of n-hexane-acetone (6:4 by volume) was passed through the column, and the fractions eluted between 0.5 liter and 0.75 liter [confirmed by thin layer chromatography (n-hexane-acetone, 1:1 by volume)] were collected and concentrated to dryness to obtain a white powder. This powder was dissolved in 50 ml of ethyl acetate, washed successively with the equal volume of diluted hydrochloric acid solution, water, saturated aqueous sodium carbonate, and water (twice in each time), and the ethyl acetate layer was dried over sodium sulfate, and concentrated to dryness. The powder obtained was dissolved in a small volume of acetone, and subjected to gel chromatography on a Sephadex LH-20 column (commodity name, produced by Pharmacia), and the column was eluated with acetone. The obtained active fractions were collected and concentrated to dryness to obtain a white powder, which was crystallized from a mixed solvent of n-hexane-acetone (4:1 by volume) to obtain 173 mg of the sodium salt of Antibiotic TM-531 B as colorless prisms.

Melting point: 252.1°–253.3° C.

On the other hand, after elution with the mixed solvent of n-hexane-acetone (6:4) in the above procedure, the fractions eluted between 1 liter and 2.5 liter [confirmed by thin layer chromatography (n-hexane-acetone, 1:1 by volume)] were also collected and concentrated to dryness to obtain a white powder. This powder was dissolved in 50 ml of ethyl acetate, washed successively with the equal volume of diluted hydrochloric acid solution, water, saturated aqueous sodium carbonate, and water (twice in each time), and the ethyl acetate layer was dried over sodium sulfate, and concentrated to dryness. The obtained powder was dissolved in a small volume of acetone, and subjected to gel chromatography on a Sephadex LH-20 column (commodity name, produced by Pharmacia) and the column was eluated with acetone. The obtained active fractions were collected and concentrated to dryness to obtain a white powder, which was crystallized from a mixed solvent of n-hexane-acetone (4:1 by volume) to obtain 222 mg of the sodium salt of Antibiotic TM-531 C as colorless prisms. Melting point: 190.4°–191.6° C.

While the invention has been described in detail and with reference to specific embodiments thereof, it will be apparent to one skilled in the art that various changes and modifications can be made therein without departing from the spirit and scope thereof.

What is claimed is:

1. A compound of the formula

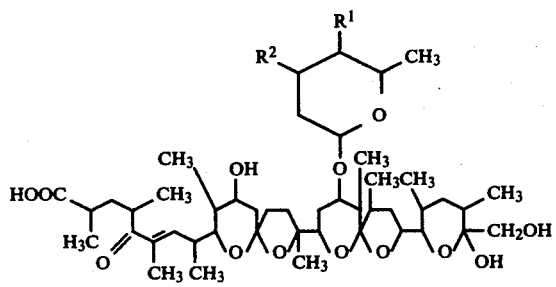
wherein either (a) $R^1$ is hydroxy and $R^2$ is hydrogen, or (b) $R^1$ is methoxy and $R^2$ is hydroxy, and the salt thereof.
2. A compound as claimed in claim 1, wherein $R^1$ is hydroxy and $R^2$ is hydrogen, and the salt thereof.
3. A compound as claimed in claim 1, wherein $R^1$ is methoxy and $R^2$ is hydroxy, and the salt thereof.
* * * * *